United States Patent [19]

Bennett

[11] Patent Number: Plant 6,135

[45] Date of Patent: Mar. 29, 1988

[54] MINIATURE ROSE PLANT 'BREAD 'N BUTTER'

[76] Inventor: Cecilia L. D. Bennett, 489 Minot Ave., Chula Vista, Calif. 92010

[21] Appl. No.: 825,457

[22] Filed: Feb. 3, 1986

[51] Int. Cl.[4] ..... A01H 5/00

[52] U.S. Cl. ..... Plt./7

[58] Field of Search ..... Plt. 7

*Primary Examiner*—James R. Feyrer

[57] ABSTRACT

The subject of the present disclosure is a new and distinct variety of miniature rose plant, named 'Bread 'n Butter', which is characterized by its blooms of bright orange with softer orange to pale yellow reverse, usually borne one to a stem with hybrid tea form. The bush is average height for a miniature, well-branched and produces moderate to heavy quantities of bloom.

1 Drawing Figure

The present invention relates to a new and distinct variety of a hardy, dwarf, bush plant of the miniature class; the variety being primarily characterized as a orange blend.

The variety is further characterized by:

Long stemmed blooms of hybrid tea-type form, borne usually one to a stem but on occasion in sprays of 3 to 5 or more. The blooms are held very erect and well above the foliage.

It has a slight fragrance.

The plant ranges in height from 15 to 24 inches (40 to 60 cm). The canes are sturdy and erect with moderate branching and medium to heavy foliage covering. The plant is a moderate to heavy bloomer that does well either in the green house or outdoors.

The plant has good growth habits, well-shaped and attractive, bearing numerous leaflets of average size.

The seed parent was Arizona (U.S. Plant Pat. No. 3,568), and the pollen parent was Orange Honey (U.S. Plant Pat. No. 4,496). It differs from its seed parent in the following ways. It is a miniature rather than a hybrid tea. It differs from the pollen parent in the following ways. It is an upright plant with blooms supported on long stems rather than a low, spreading trailer-type of miniature with blooms on short stems. It does not mature to redder tones which is typical of its pollen parent.

The descriptive matter which follows, pertains to roses grown and color values observed in plants and newly opened blooms in the months of March through August 1985. The plants were grown outdoors in Chula Vista, Calif. and are believed to be accurate standards for this cultivar in similar conditions of soil and climate elsewhere.

The color photograph illustrates the variety.

Referring now specifically to the new and distinct variety of miniature rose plant named 'Bread 'n Butter', the following is a detailed description thereof in outline; all major color plate identifications being by reference to the British Colour Council Horticultural Colour Chart, except where common terms of color definition are employed.

Type: Hardy, dwarf, bushy, green house or outdoor, decorative potted plant.

Class: Miniature.

Asexual reproduction: I have found this variety to be easily asexually reproduced by cuttings.

Variety name: Bread 'n butter.

Flowers borne: Usually one to a stem, but occasionally in sprays of 3 to 5 or more on erect stems with foliage well below the blooms.

Quantity of bloom: Moderate to heavy both outdoors or green house grown.

Bud:

*Peduncle.*—Variable in length (20 to 60 mm); average diameter and sturdy; ranging from near Lettuce Green (861 to 861/2 page 176) to near Scheeles Green (860 to 860/2 page 175) with some tinting of bronze.

*Hairs.*—Extremely small and numerous with a reddish color: located over the entire surface of the peduncle and sepals, but not present on the calyx tube.

*Calyx.*—Color ranging from near Lettuce Green (861 to 861/3 page 176) to near Scheeles Green (860 to 860/3 page 175).

*Opening.*—Opens well in all weather.

Bloom:

*Size when fully open.*—Average for a miniature variety (40 to 50 mm).

*Petalage.*—Full — averaging 40 to 50 petals, arranged regularly, plus 10 to 20 petaloids or more.

*Form.*—Urn-shaped to ovoid as the bloom progresses. The petals remain at first somewhat tightly cupped with the apex and/or margins reflexed outward, becoming at maturity more loosely cupped; and the petals reflexed more tightly (quilling), until each row of petals forms a five pointed star.

Petals: Fairly thick with good substance; both the upper and under surfaces of all petals have a matte finish.

*Shape.* —Outer petals are of a very broad obovate form. The intermediate petals are very much like the outer petals only narrower. The inner petals are a broad lanceolate form; and the petaloids are also lanceolate form with some occasional irregularities.

Color: Newly opened flowers from plants grown outdoors (March through August 1985), Chula Vista, Calif.

*Outside petals.*—Upper surface — Base of near Canary Yellow (2/2 to 2 page 2); body of near Nasturtium Orange (610/2 to 610 page 145); margin of near Nasturtium Orange (610/3 to 610/2 page 145) with occasional apex of near Egyptian Buff (407/3 page 122). Under surface — Near Nasturtium Orange (610/2 to 610/3 page 145) with a base of near Canary Yellow (2/3 page 2).

*Intermediate petals.*—Upper surface — Base of near Canary Yellow (2/1 to 2 page 2); body and margins of near Nasturtium Orange (610 to 610/1 page 145). Under surface — Near Indian Yellow (6 to 6/1 page 6) over entire surface.

*Inner petals.*—Upper surface — Near Cadmium Orange (8 to 8/1 page 8) with a base of near Canary Yellow (2 to 2/1 page 2). Under surface — Near Indian Yellow (6/1 to 6/2 page 6) over entire surface.

*General color effect.*—Newly opened flowers bright Nasturtium Orange with reverse of softer shades of orange and yellow. Three days open — Some fading of the tones of orange and yellow. Five to seven days — Petals continue to fade with occasional blushing of outermost petals. Quilling effect present on all petals. After 7 days — Petals faded to soft tones of orange and yellow, all petals quilling to with some outer petal margins soft Egyptian Buff to near cream.

*Flower longevity.*—(March through August 1985) Plant in pot 4 to 7 days from bud with sepals reflexed to fully opened bloom. Holding at fully opened with gradual fading of orange and yellow tones for 5 to 7 days or longer. Cut blooms at living room temperature 3 to 5 days or longer.

Reproductive organs:

*Stamens.*—A generous amount arranged uniformly around the pistil.

*Filaments.*—Varying in length with shorter filaments more proximal to the pistil; pale yellow in color with golden yellow anthers.

*Pollen.*—Abundant.

*Pistil.*—Long, abundant and spreading; reddish styles with pale yellow caps.

*Ovaries.*—All encased in calyx.

*Hips.*—Some; color near Cadmium Orange (8 to 8/2 page 8); globular in form.

*Seeds.*—Approximately 1 to 25 per hip.

*Sepals.*—Permanent; spear-shaped; open as the bloom opens, eventually recurves as the peduncle.

Foliage:

*Leaves.*—Five to seven leaflets on the average; medium size for a miniature rose plant.

*Leaflets.*—Broad ovate-shaped.

*Margin.*—Very serrated with occasional tinting of bronze, especially noticeable on the newer foliage.

*Color.*—Ranging from near Spinach Green (0960 to 0960/2 page 187) to near Scheeles Green (860 to 860/2 page 175) on the newer foliage with occasional bronzing of the margins, especially of the newer foliage. The upper surfaces have a semi-glossy finish, and the under surfaces have a matte finish of a slightly lighter shade than the upper surfaces.

*Rachis.*—Medium strength; upper surface is grooves with very small hair over the length of it. Under surface has few if any hairs but does contain 2 to 5 small thorns.

*Stipules.*—Varying in length from small to average width; tapering auricles angled outward at about 45 degrees.

Growth:

*Habit.*—Dwarf, bushy; average height for a miniature rose plant.

*Growth.*—Moderate and well-branched.

*Canes.*—Medium diameter; sturdy; held erect.

*Main stems.*—Color — Ranging from near Scheeles Green 860 to 860/2 page 175) to near Spinach Green (0960 to 0960/3 page 187).

*Thorns.*—Averaging 5 to 10 per 10 cm on the main stems and fewer on the branches. Reddish in color with occasional tinting of bronze. Small to average in size. Slender and hooked slightly downward.

*Branches.*—Color — Same as main stems.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant named, 'Bread 'n Butter' of hardy, dwarf, moderate growth, well-branched and attractive appearance, substantially as illustrated and described, characterized by its blooms of bright Nasturtium Orange with softer orange and yellow reverse, with flowers borne usually one to a stem, but occasionally in sprays of 3 to 5 or more.

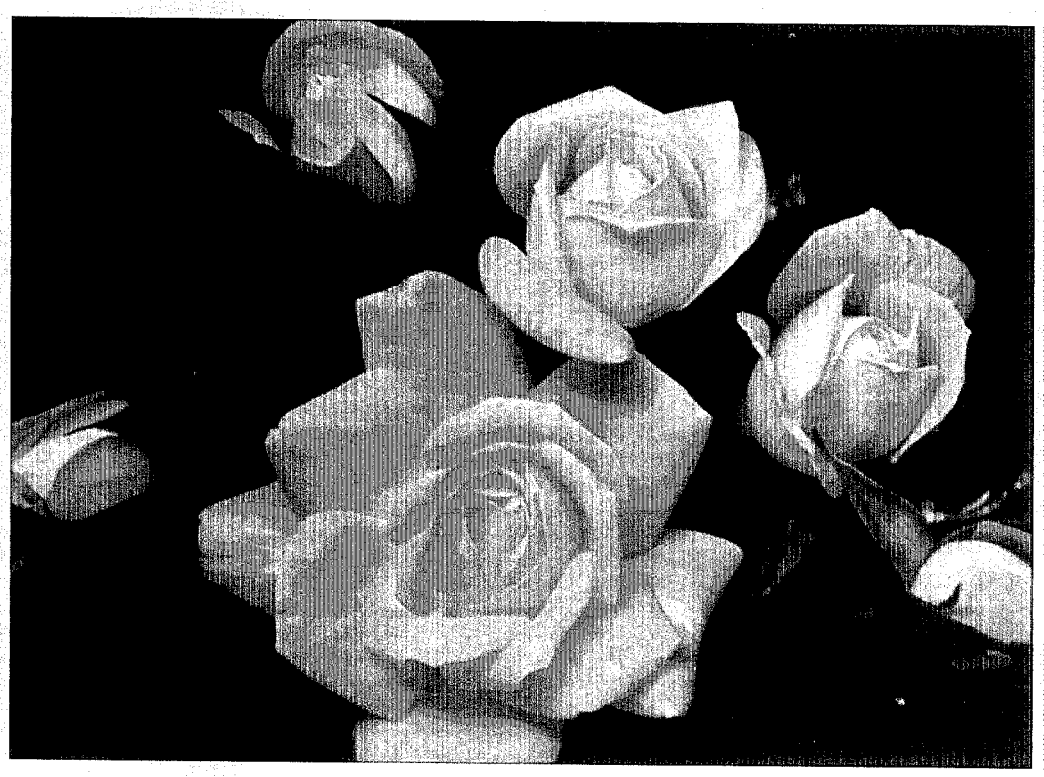

* * * * *